United States Patent
Mombrun et al.

(10) Patent No.: US 11,002,733 B2
(45) Date of Patent: May 11, 2021

(54) LATERAL FLOW DEVICE COMPRISING SAMPLING

(71) Applicants: COMMISSARIAT A L'ENERGIE ATOMIQUE ET AUX ENERGIES ALTERNATIVES, Paris (FR); SOCIETE DES SYSTEMES BIOLOGIQUES, Apprieu (FR)

(72) Inventors: Adrien Mombrun, Grenoble (FR); François Berger, Meylan (FR); Mohamed-Ali Bouamrani, Grenoble (FR); Gary Brandam, Irigny (FR); Clarence Deffaud, Voiron (FR); Julien Roux, Voiron (FR)

(73) Assignees: COMMISSARIAT A L'ENERGIE ATOMIQUE ET AUX ENERGIES ALTERNATIVES, Paris (FR); SOCIETE DES SYSTEMES BIOLOGIQUES, Apprieu (FR)

( * ) Notice: Subject to any disclaimer, the term of this patent is extended or adjusted under 35 U.S.C. 154(b) by 412 days.

(21) Appl. No.: 15/739,557

(22) PCT Filed: Jun. 24, 2016

(86) PCT No.: PCT/IB2016/053766
§ 371 (c)(1),
(2) Date: Dec. 22, 2017

(87) PCT Pub. No.: WO2016/207842
PCT Pub. Date: Dec. 29, 2016

(65) Prior Publication Data
US 2018/0188248 A1    Jul. 5, 2018

(30) Foreign Application Priority Data

Jun. 25, 2015 (FR) .................... 1555890

(51) Int. Cl.
*G01N 21/75* (2006.01)
*G01N 31/22* (2006.01)
(Continued)

(52) U.S. Cl.
CPC ...... *G01N 33/54386* (2013.01); *B01L 3/5023* (2013.01); *G01N 33/558* (2013.01);
(Continued)

(58) Field of Classification Search
CPC .......... G01N 33/54386; G01N 33/558; G01N 21/75; G01N 31/22; G01N 33/52;
(Continued)

(56) References Cited

U.S. PATENT DOCUMENTS 6,780,584 B1 * 8/2004 Edman .............. B01J 19/0046
422/50
2002/0036170 A1   3/2002 Harvey
(Continued)

FOREIGN PATENT DOCUMENTS

BE    1011487    10/1999
FR    2614423    10/1988
(Continued)

*Primary Examiner* — Brian J. Sines
(74) *Attorney, Agent, or Firm* — Lex IP Meister, PLLC

(57) ABSTRACT

The invention relates to a lateral flow device (10) for taking at least one analyte of interest in a fluid, comprising:
- a fluid receiving zone (100) for receiving the fluid, comprising a first absorbent material (111) that is capable of collecting the fluid;
- at least one zone of migration (201) for migration of the fluid, extending between a first end and a second end, each zone of migration including a draining material (211) in fluid continuity with the first absorbent material;
- at least one fluid reservoir (storage) zone (301) comprising a second absorbent material (311) in contact with the draining material at the level of the second end of each fluid migration zone;

(Continued)

the detection means between the receiving zone and the reservoir zone, that provide the ability to determine the presence or absence of the said one or more analyte(s) of interest in the sample;

characterised in that at least the one of the said zones of migration further also comprises at least one capture zone (400) that is capable of receiving a capture element (411) applied against the draining material between the first end and the second end thereof.

20 Claims, 12 Drawing Sheets

(51) Int. Cl.
  *G01N 33/52* (2006.01)
  *G01N 35/00* (2006.01)
  *G01N 33/543* (2006.01)
  *G01N 33/558* (2006.01)
  *B01L 3/00* (2006.01)

(52) U.S. Cl.
  CPC ..... *B01L 2200/10* (2013.01); *B01L 2300/069* (2013.01); *B01L 2400/0406* (2013.01)

(58) Field of Classification Search
  CPC ... G01N 35/00; B01L 3/5023; B01L 2200/10; B01L 2300/69; B01L 2400/0406
  USPC ............... 422/68.1, 412, 413, 419, 420, 425
  See application file for complete search history.

(56) References Cited

U.S. PATENT DOCUMENTS

| | | | |
|---|---|---|---|
| 2005/0112729 A1* | 5/2005 | Kira | C12P 13/04 |
| | | | 435/106 |
| 2006/0019404 A1 | 1/2006 | Blatt | |
| 2012/0308444 A1 | 12/2012 | Zhu | |
| 2013/0052669 A1* | 2/2013 | Paulovich | G01N 33/5306 |
| | | | 435/7.92 |
| 2014/0273269 A1* | 9/2014 | Liu | G01N 33/558 |
| | | | 436/501 |
| 2015/0309008 A1* | 10/2015 | Adelman | A61B 5/02055 |
| | | | 356/72 |

FOREIGN PATENT DOCUMENTS

| | | |
|---|---|---|
| FR | 2853077 | 10/2004 |
| FR | 2881828 | 8/2006 |
| FR | 2967497 | 5/2012 |
| WO | 9610179 | 4/1996 |
| WO | 9734150 | 9/1997 |
| WO | 2004067162 | 8/2004 |
| WO | 2007023372 | 3/2007 |
| WO | 2009003177 | 12/2008 |
| WO | 2013140089 | 9/2013 |

\* cited by examiner

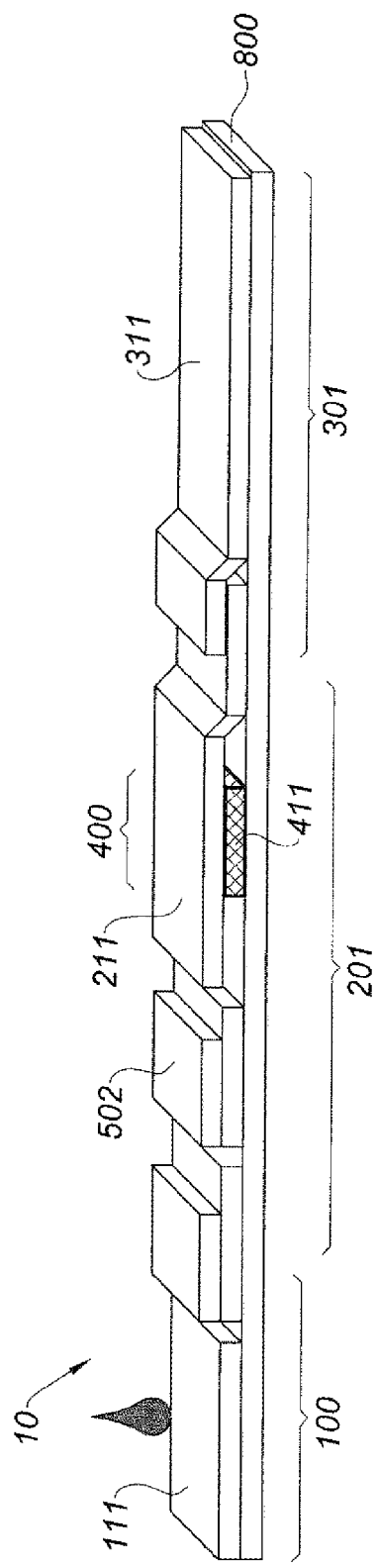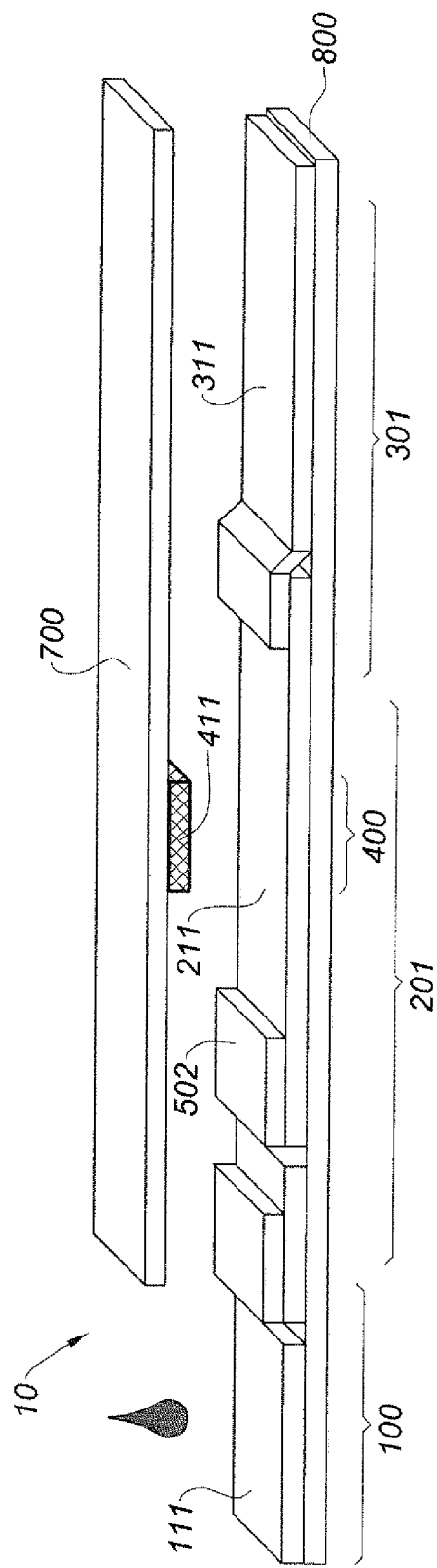

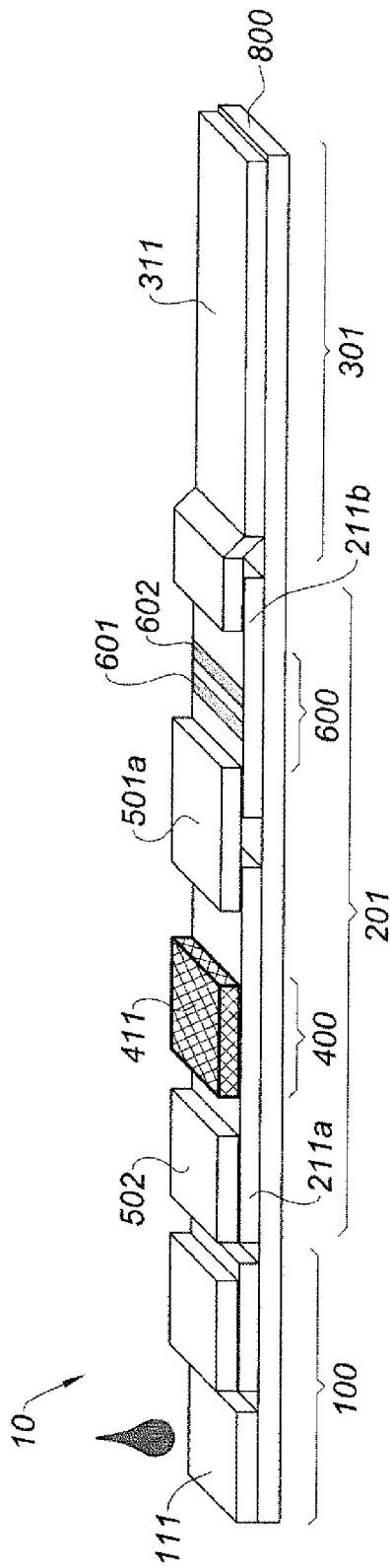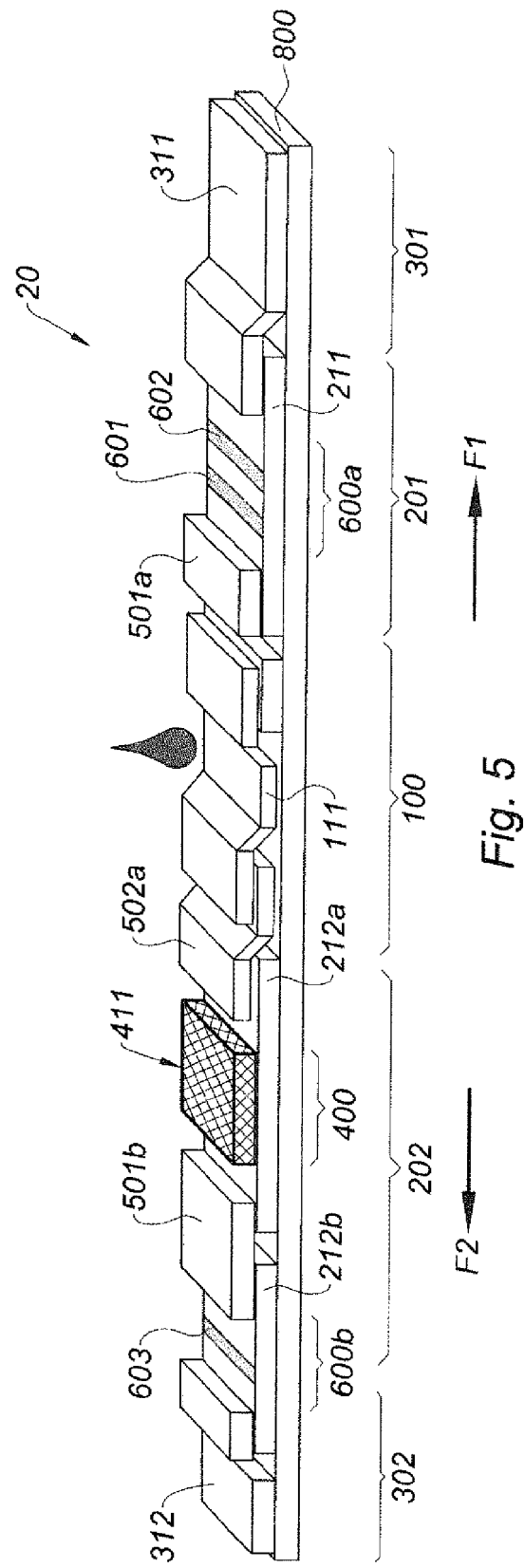

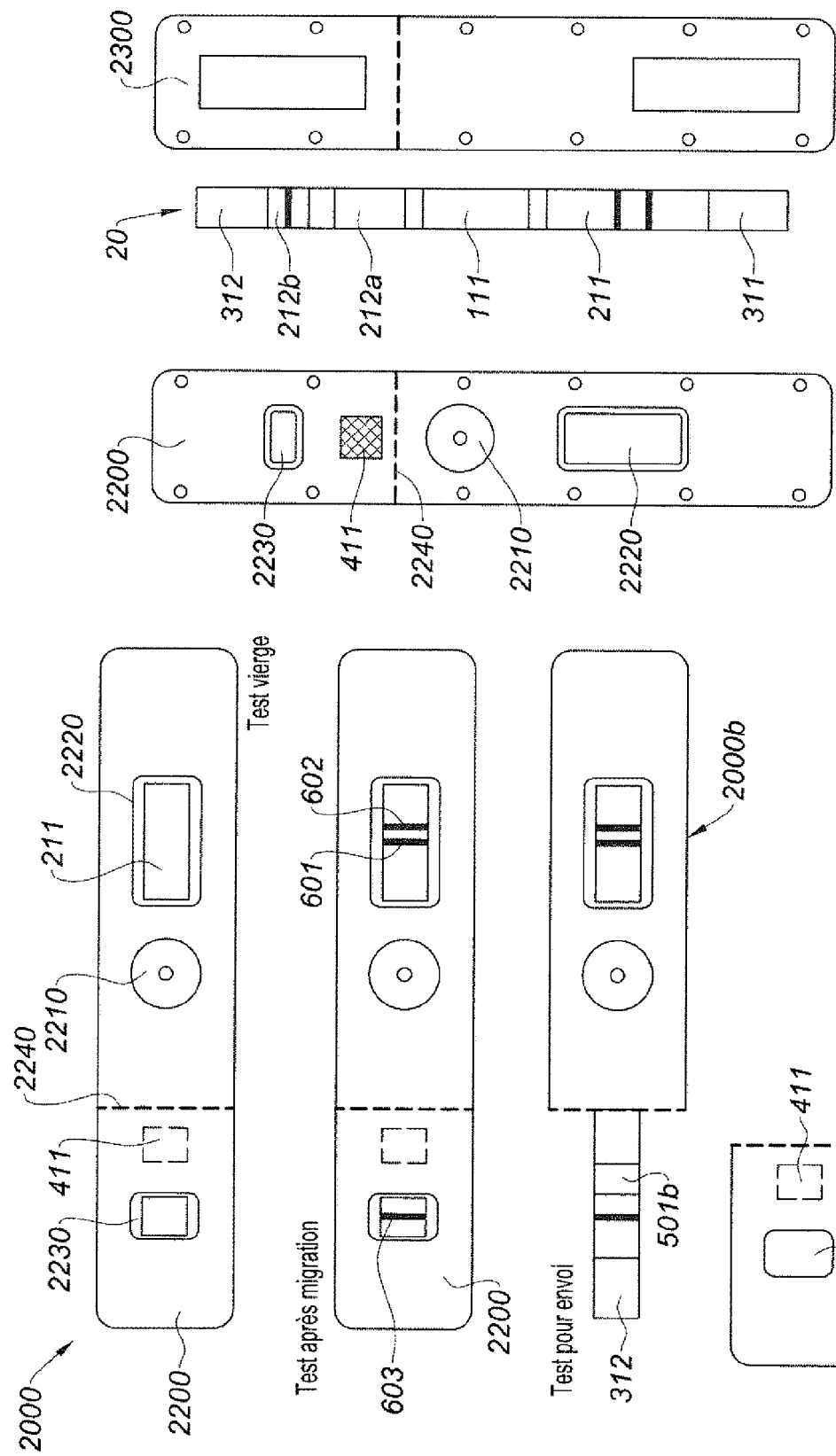

LATERAL FLOW DEVICE COMPRISING SAMPLING

The invention pertains to the field of single—use devices for rapid and qualitative diagnosis.

Conventional lateral flow devices allow for the colorimetric detection of analytes present in a fluid. These devices make use of an absorbent material, through which the fluid to be analysed migrates. They are particularly suitable for the in situ collection of a body fluid, the filtration of this fluid (for example in the case of blood, the removal of erythrocytes), as well as for the qualitative analysis of the fluid, that is to say, the determining of initial information in respect of the presence or absence of a certain amount of a given analyte in the fluid.

From the document US 2002/0036170 a lateral flow device designed for separating red blood cells from blood plasma is already known. The device includes a pad on which is deposited a lateral flow chromatographic membrane; it comprises, at a first end of the membrane, a sample application zone, followed by a capture zone comprising a binding agent for binding with erythrocytes, and then a capture zone at a second end. The goal is to capture one or more protein(s) of interest in the capture zone with a view to performing an analysis either visual (qualitative), or by means of sampling of a portion of membrane in the capture zone (quantitative).

The document US 2012/0308444 discloses a lateral flow device designed for simultaneously identifying the presence of two proteins in one fluid sample. The device includes a pad on which is deposited a lateral flow chromatographic nitrocellulose membrane; it comprises on the membrane successively, a sample application zone, a first and then a second conjugate zone, a first reading line for visibly revealing the presence of the first protein, a second test line for revealing the presence of the second protein and a control line for visibly revealing that the fluid has passed beyond the two test lines.

The document US 2006/0019404 discloses a lateral flow device that provides the ability to perform a measurement that is at least partially quantitative of an analyte of interest through the use of different test zones, having different sensitivities. A quantitative measurement of concentration of human chorionic gonadotropin (hCG) is obtained by measuring the reflectance of the colour blue obtained in the capture zone.

Such devices are not compatible with the methods for precise quantitative analyses, such as mass spectrometry.

Also, it is sought to provide for a device which, while allowing for a qualitative measurement (for example, a change in colour when an analyte is present in the fluid), also makes it possible to associate or combine therewith a quantitative measurement (an assay), in particular when the qualitative measurement leads to a suspicion of the presence of a particular analyte.

In addition, it is sought to provide an appropriate device that is suitable for use in situ, at the bedside of the ill if necessary and without the need for special equipment at the place of use thereof, and which despite the latter, makes it possible to carry out, from the same sample, a quantitative and precise molecular analysis, possibly time resolved in relation to the time instant of the sample collection. This implies that the sample has been stabilised.

In order to resolve these difficulties, the invention provides a lateral flow device for the sampling of at least one analyte of interest in a fluid sample, which includes:

A fluid receiving zone for receiving the fluid, comprising a first absorbent material that is capable of collecting the fluid;

At least one zone of migration for migration of the fluid, extending between a first end and a second end, each zone of migration including a draining material in fluid continuity with the first absorbent material, the draining material being capable of collecting the fluid absorbed by the receiving zone and of draining the fluid from its first end to its second end;

At least one fluid reservoir (storage) zone, comprising a second absorbent material, in contact with the draining material at the level of the second end of each fluid migration zone, the second absorbent material being capable of absorbing the fluid drained by the draining material;

The detection means between the receiving zone and the reservoir zone, that provide the ability to determine the presence or absence of the one or more analyte(s) of interest in the sample;

in which at least one of the zones of migration also comprises at least one capture zone that is capable of receiving a capture element applied against the draining material between the first end and the second end thereof. The term "analyte of interest" is used to refer to an analyte whose presence in the fluid is sought to be detected. It may be a protein, an organic molecule, a drug, a toxin, a nucleic acid, a sugar, a lipid, traces of micro-organisms or parasites, etc.

The term "fluid sample" is used to refer to any type of fluid sample originating from an environment to be analysed, and in particular any type of body fluid sample such as blood, plasma, serum, urine, ascitic fluid, pleural fluid, pericardial fluid, synovial fluid, or bronchoalveolar lavage. Environmental fluids such as effluents, can also be analysed by using a device according to the present invention.

The term "in fluid continuity" is used to refer to the fact that the absorbent material and the draining material are arranged in a manner such that the fluid deposited on the first absorbent material can move forward by capillary action towards and into the draining material. For example these materials are directly in contact, or they are connected by another material through which the fluid may also move forward by capillary action.

Advantage is taken of the filtration capabilities of the first absorbent material and of the draining material in a manner such that the larger particles or cells present in the fluid are removed therefrom at the time that it reaches the capture zone. Thus, the collection yield of analytes of interest, and in particular of small molecules, is optimised, and compatible with a direct mass spectrometry reading. Experience shows that the position of the capture zone, and therefore of the capture material, between the receiving zone and the reservoir zone has an effect on the nature, in particular influencing the size of the analytes collected and enriched on the capture material (this is illustrated by Example 1 here below).

The invention does not in any way preclude the device from comprising multiple capture zones, in particular two capture zones, especially when it includes two migration zones.

Advantageously, the device may in addition comprise a capture element that is applied on to each capture zone, each capture element being capable of capturing an analyte of interest present in the fluid.

In this configuration, the capture element is applied on to the capture zone of the draining material.

Advantageously, each capture element may comprise a nanoporous or mesoporous material.

The capture element may be made of any absorbent material, but advantageously it may comprise a nanoporous or mesoporous material, for example nanoporous or mesoporous Silicon. This material has the advantage of being able to retain the analytes of interest that are trapped for several days without them undergoing degradation (this is illustrated by Example 2 here below).

Advantageously, the detection means may include:

At least one conjugate material disposed to be in contact with the draining material, the conjugate material comprising conjugate particles that are capable of binding to the analyte(s) of interest;

A material that is capable of immobilising the conjugate particles bound to an analyte of interest and of revealing them, the said material impregnating a zone of detection of the draining material.

Such a conjugate material (or conjugate pad) may be disposed astride two separate segments of the draining material in order to ensure that it is traversed through by the fluid.

The conjugate particles may in particular be microbeads functionalised in a manner so as to bind to the analyte(s) of interest.

The detection zone is a zone of the draining material impregnated with a material that is capable of immobilising the conjugate particle bound to an analyte of interest, situated downstream from the conjugate material in the direction of drainage of the fluid. The conjugate particles are generally coloured or fluorescent, such that when the fluid contains a certain quantity of analytes of interest, the detection zone captures the said analytes grafted on to the microbeads and thus changes its appearance. It is then possible to obtain a colorimetric, qualitative reading, that is representative of the quantity of analyte of interest in the sampled fluid. The excess of the conjugate particles is drained to the reservoir zone.

In a second embodiment, the device may comprise a first zone and a second zone of migration respectively including a first draining material and a second draining material, the receiving zone being situated between the said two zones of migration.

The receiving zone is in fluid contact with the first end of each zone of migration, each reservoir zone being in contact with the second end of a respective zone of migration. When the sample is deposited on the receiving zone, the fluid diffuses on either side of this zone. A first portion of the fluid is used for a qualitative detection, for example colorimetric detection, and a second portion of the fluid is absorbed by the capture material, which may be analysed in case of positive detection.

The first and second draining materials may be identical or different.

Advantageously, the first absorbent material and/or the second absorbent material may be made of a fibrous material.

Advantageously, the receiving zone may comprise, in addition to the first absorbent material, a transfer material.

This transfer material then ensures the fluid continuity between the first absorbent material and a draining material.

Advantageously, at least one of the draining materials may comprise a nanoporous or mesoporous material. The fact that this material is not fibrous makes it possible for the fluid to advance along a substantially rectilinear front.

Advantageously, the capture zone may be located upstream from the conjugate zone in the direction of drainage of the fluid in the draining material. It is thus ensured that the capture material will not be polluted by the conjugate particles.

Advantageously, at least one of the conjugate materials may include conjugate particles that are capable of binding to an analyte which is certain to be found in the fluid.

In this way, the detection of these conjugate particles in the detection zone, preferably situated downstream from the capture zone, makes it possible to ensure that the fluid has been exposed to the capture element.

Advantageously, the first absorbent material, each draining material, and the second absorbent material are disposed on a support or carrier material.

The carrier material is preferably made out of a non-absorbent material, in a manner such as to channel the migration of the fluid.

Advantageously, the device may further also include a cover material that is capable of covering at least a portion of the receiving zone, the zone of migration and/or the fluid reservoir (storage) zone.

The function of this cover material is to isolate the device from the environment, in a manner so as to prevent inadvertent contamination. In this case, a capture element may be maintained between the cover material and the drainage material.

Advantageously, the capture element may be adapted so as to be separated from the draining material.

This makes it possible to detach the capture element in order to send it to a laboratory with a view to performing a quantitative analysis of the analyte desired.

The capture element and the first absorbent material may be disposed on the same surface or on two opposite surfaces of the draining material.

The act of combining, on a same given device, a colorimetric detection zone and a capture element makes it possible to have a first qualitative analysis, indicating a possibility of presence of an analyte of interest. It is then possible to detach the capture element and to analyse it by making use of a quantitative method of a type such as mass spectrometry, possibly on time resolved basis, in order to provide for an accurate assay of the analyte of interest as well as, possibly, an assay of other analytes.

Advantageously, the capture element may be maintained in place against the draining material.

The term "maintained in place against the draining material" is used to refer to the fact that the capture element is not separable from the draining material, without at least partially destroying the device. This is for example the case when the capture element is interposed between the draining material and the carrier material, or between the draining material and the cover material. In this case, the capture element is not necessarily detached from the device in order to be sent to an analysis centre that possesses the quantitative analysis means; the device can in fact be sent wholly intact.

The invention also relates to a sampling system for sampling analytes of interest in a fluid, characterised in that it includes an enclosure wherein is located a lateral flow device according to the invention, and comprising a single zone of migration, the enclosure including:

a first opening disposed so as to be facing the receiving zone of the device;

a first window disposed so as to be facing the detection zone in order to ensure the ability to read a detection signal.

The invention also relates to a sampling system for sampling analytes of interest in a fluid, characterised in that it includes an enclosure wherein is located a lateral flow device according to the invention, comprising two zones of migration, the enclosure including:
- a first opening disposed so as to be facing the receiving zone of the device;
- a first window disposed so as to be facing the first detection zone in order to ensure the ability to read a first detection signal;
- a second window disposed so as to be facing the second detection zone in order to ensure the ability to read a second detection signal.

In this manner the operator no longer needs to touch the device in the handling thereof, which reduces the risk of contamination that would be attributable to this handling.

Advantageously, the enclosure may in addition comprise a second opening disposed so as to be facing a capture zone of the device, in a manner such as to be able to deposit a capture element on to the capture zone and/or to remove it therefrom.

The capture element is thus deposited on the draining material, at the level of the capture zone, through the second opening.

The enclosure may also comprise at least one position indicator for the purpose of guiding the user in the depositing of the capture element on the draining material, for example in the form of graduations, these indicators being used as reference markers for the positioning of the capture material. The capture material will be all the more distant from the receiving zone given that it is sought to collect small sized analytes.

The first window and the second opening may be combined into one single opening.

According to a first alternative, the device may further also comprise at least one capture element maintained in place on the capture zone, each capture element being capable of capturing an analyte of interest present in the fluid.

In this case, the capture element may not be easily detached from the draining material and the entire system, enclosure and device, is preferably sent to the analysis centre.

According to a second alternative, the capture element may be attached to a detachable support that is detachable from the enclosure.

In this case, the detachable support of the enclosure may be one of the following elements:
- A plate that is capable of being secured at least temporarily on to the edges of the second opening;
- A cleavable part of the enclosure;
- A cap that is capable of being secured both on a capsule and on the second opening. In this case, only the detachable support is sent to the analysis centre.

The present invention also relates to a sampling method for sampling at least one analyte of interest in a sample by making use of a device or a system as described here above, that includes the following steps:
- depositing the sample on the receiving zone of a lateral flow device; and
- waiting until the fluid has migrated to the fluid reservoir (storage) zone, in which, in case of the presence of the analyte of interest in the sample, as evidenced by the detection means, the said analyte is drawn into the capture element.

When this sampling method is carried out by making use of a device which provides for the separation of the capture element, either alone or attached to a support such as, for example, the cap described here above, an additional step is advantageously added, consisting, at the conclusion of the step of migration of the fluid, of separating the capture element from the rest of the device. The capture element may be then stored for a period of several weeks if necessary and/or sent to a remote laboratory in order to carry out a quantitative determination of its contents and/or introduced into an assay apparatus such as a mass spectrometry apparatus.

An assay method for assaying at least one analyte of interest in a fluid sample, comprising a sampling step for sampling of the said one or more analyte(s) by means of a sampling method as described here above, followed by a step of assaying the said one or more analyte(s) present in the capture element, is also an integral part of the invention.

A particular assay method in conformity with the invention, making use of a system as described here above, includes the following steps:
- depositing the said sample on the first opening of the enclosure;
- waiting for the period of time necessary for migration of the fluid to the detection zone;
- reading a result that establishes that the fluid sample has migrated beyond the capture zone and, if possible, that the analyte of interest is indeed present in the sample; and
- carrying out the assay of at least one analyte of interest from the quantity of analyte captured by the capture element.

According to another assay method in conformity with the invention, the method is carried out by making use of a system in which the capture element is attached to a detachable support of the enclosure such as a plate or a cap; the method then includes the following steps:
- where appropriate (if the system is provided with the capture element initially separated from the rest), applying the capture element on to the capture zone of the draining material, by making use of the detachable support;
- depositing the said fluid sample on the first opening of the enclosure;
- waiting for the period of time necessary for migration of the fluid to the detection zone;
- reading a result that establishes that the fluid sample has migrated beyond the capture zone;
- detaching the detachable support of the enclosure, and
- carrying out the assay of at least one analyte of interest from the quantity of analyte captured by the capture element.

According to one variant of the method described here above, in which the detachable support is a cleavable part of the enclosure, the method includes the following steps:
- depositing the said fluid sample on the first opening of the enclosure;
- waiting for the period of time necessary for migration of the fluid to the detection zone;
- reading a result that establishes that the fluid sample has migrated beyond the capture zone;
- detaching the cleavable part from the enclosure;
- proceeding to carry out the assay of at least one analyte of interest from the quantity of analyte captured by the capture element.

Some embodiments and variants are described here below by way of non-limiting examples with reference to the accompanying drawings in which:

FIGS. 2 and 3 represent in perspective two embodiments of a device in which a capture element is inseparable from the device;

FIG. 4 represents in perspective one embodiment of a device in which a capture element can be separated from the device;

FIG. 5 represents in perspective one embodiment of a device comprising two lateral flows;

FIGS. 8A and 8B represent in top view and in exploded view one embodiment of an enclosure wherein a double lateral flow device is located;

Figure 12:
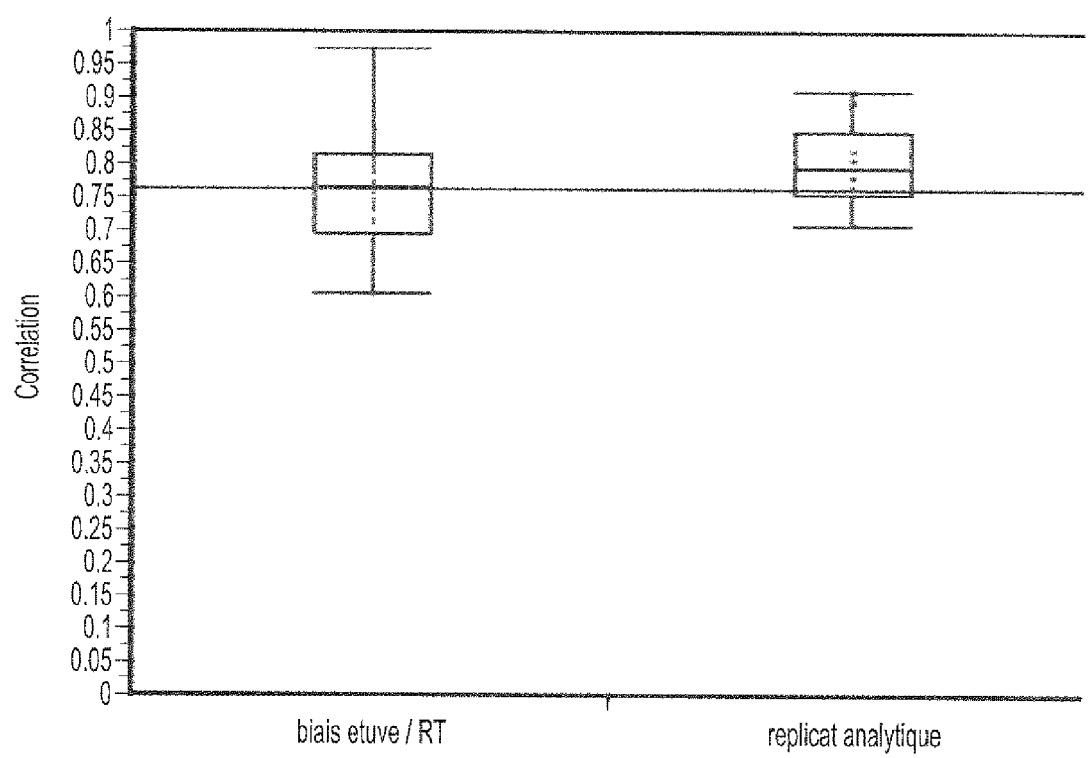
Figure 13:
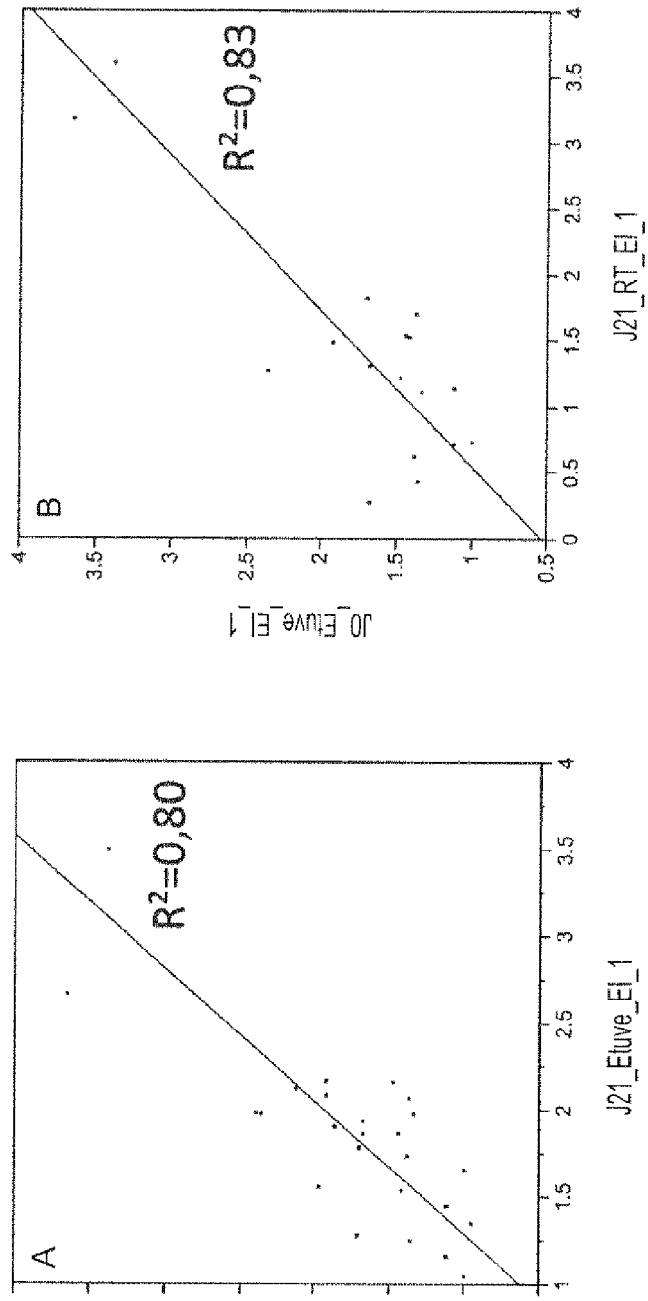

FIG. 12 represents the correlation of the spectral characteristics obtained over 21 days between the conditions of storage at ambient temperature and at 37° C. By means of oven/RT [room temperature]: Distribution of correlations for each peak detected (intensities, S/N) between 21 days at RT and 21 days at 37° C. Analytical replica: Distribution of correlations for each peak detected between analytical replica of same conditions;

FIG. 13 shows the correlation of the profiles (same detected peaks, intensities, signal/noise) between D0 and D21 at 37° C. (panel A) and between D0 and D21 at ambient temperature (panel B).

Figure 1A:
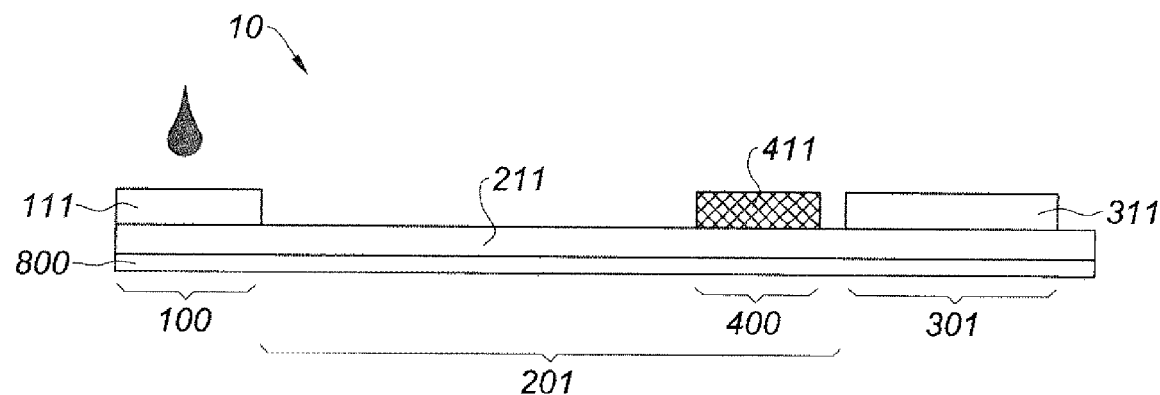
FIGS. 1A and 1B represent in elevation two embodiments of a device.

The lateral flow device 10 illustrated in FIG. 1A includes a pad of draining material 211 resting on a support 800. This draining material is preferably non-fibrous, the size of pores being comprised between 0.2 μm and 1 μm, or even between 0.2 μm and 10 μm. It may be Nitrocellulose, Acrylic, Polyethylene Sulfone, PVDF (Polyvinylidene Fluoride), PTFE (Polytetrafluoroethylene), Cellulose Nitrate, etc.

Figure 1B:
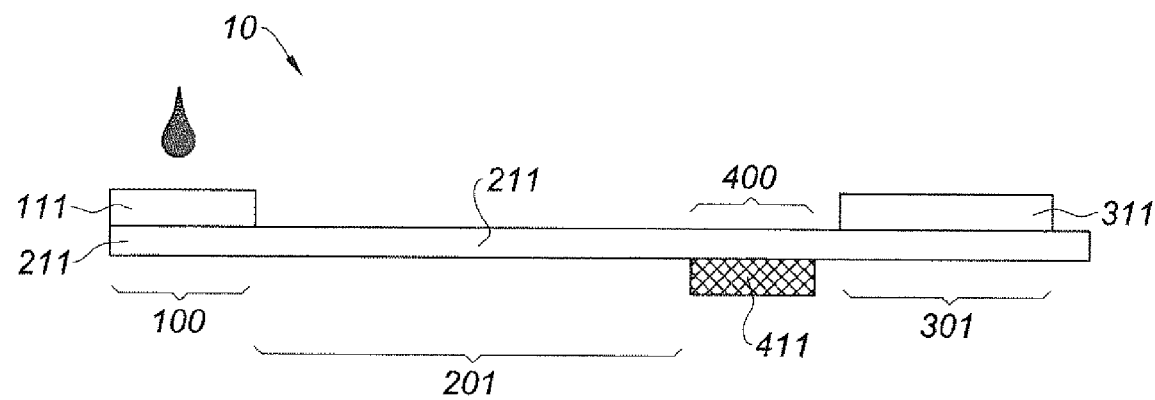

With regard to the support 800 it is made out of an impervious waterproof material, designed so as to provide a certain degree of rigidity to the draining material, for example Polypropylene, Vinyl W™, PVC (polyvinylchloride), HIPS (high impact polystyrene), polyester, etc. However this support is not absolutely essential, it being possible for the draining material to possess sufficient rigidity. FIG. 1B illustrates a device whose draining material does not comprise a support.

The device 10 possesses in succession:
- a first end, a receiving zone 100, that comprises a first absorbent material 111 disposed over and in direct contact with one surface of the draining material, provided in order to receive a fluid sample; this surface will hereinafter be referred to as upper surface of the draining material, the opposite surface being referred to as under surface;
- a zone of migration 201 of the fluid;
- at a second end, a reservoir zone 301, comprising a second absorbent material 311 disposed over and entirely in contact with the upper surface of the draining material, that is provided in order to absorb the excess fluid having traversed through the draining material.

In this manner, the first absorbent material, the draining material and the second absorbent material are in fluid continuity: the fluid deposited on the first absorbent material 111 penetrates by capillary action into the draining material 211 and advances along this draining material to the second absorbent material 311. As will be seen here below, other arrangements make it possible to ensure this fluid continuity.

The first and second absorbent materials 111, 311 are for example made of cellulose fibre, glass fibre, Polyvinyl Sulfone, etc. These materials preferably present a disordered structure (fibres) or an ordered structure (mesh), in a manner so as to enable filtration of the fluid, in the receiving zone 100, while retaining in particular the cellular organisms and debris in the case, for example, of biological fluids such as blood (erythrocytes, leukocytes, platelets) or urine (debris, bacteria), upstream of the zone of migration 201. On the same given device, the said first and second absorbent materials may be identical or different.

The first absorbent material 111 may have been subjected to a pretreatment by impregnation in a solution and then drying, in a manner so as to enable a conditioning of the fluid at the level of the receiving zone 100, for example alteration of the pH, additions of ions, additions of internal calibrant for quantitative molecular analysis, anticoagulants, stabilisers, anti-proteases, etc.

The volume of the second absorbent material 311 is generally greater than the respective volumes of the first absorbent material 111 and of the draining material 211, in a manner such that its absorptive capacity is greater than the absorptive capacity of the first absorbent material 111 and of the draining material 211. Thus, the reservoir zone 301 fulfills the function of capillary pump, making possible a fluid flow between the receiving zone 100 and the reservoir zone 301.

The zone of migration 201 comprises a capture zone 400; as is represented in FIGS. 1A and 1B, a capture element 411 is disposed on this capture zone, in contact with the draining material 211. As illustrated, the capture element 411 may be disposed on the upper surface or on the under surface of the draining material 211.

The capture element 411 is provided in order to capture one or more analytes of interest during the course of their migration in the draining material from the receiving zone to the reservoir zone.

In the embodiments illustrated, the capture element 411 is made out of nanoporous silicon or mesoporous silicon; as illustrated in Example 2 here below, this material presents the advantage of being able to retain the analytes of interest for a period of several days without degradation.

The capture element 411 is detachable from the draining material 211 in order to allow for a quantitative analysis of the one or more analytes of interest such as proteins, metabolites, organic molecules, etc.

In a first embodiment, the capturing element 411 is entirely movable, that is to say, it is applied by the operator on to the capture zone 400 of the draining material 211 at the time of the sampling and then it is detached so as to be sent to an analysis centre for assaying of the one or more analytes interest. In other embodiments, the capture element is integrally attached to the device, the latter being detached from the draining material only at the time of the quantitative assay.

FIG. 2 illustrates another embodiment of the device 10 in which:

- the capture element 411 is maintained in place between the support 800 and the draining material 211, it is thus in contact with the under surface of the draining material; in this embodiment, the device 10 at the very outset comprises the capture element 411;
- the receiving zone comprises a transfer material 502 which is interposed between the first absorbent material 111 and the draining material 211, while also ensuring the fluidic continuity between these two materials; the said transfer material makes possible for example the filtration of the formed elements of the blood; and is made of a fibrous material, defining a mesh, whether ordered or not ordered, whose average size is less than the size of the meshes of the first absorbent material 111 in order to allow for the capillary pumping of the fluid originating from the said first material.

In the practical implementation, the first absorbent material 111 partially overlaps the transfer material 502, which in its turn partially overlaps the draining material 211. At the other end of the device, the second absorbent material 311 partially overlaps the draining material 211. This thus ensures the fluid continuity between the receiving zone 100 and the reservoir zone 301. The fluid advances by capillary action in the direction of the arrow F1.

FIG. 3 illustrates another embodiment of the device 10 comprising a cover material 700 that partially covers the first absorbent material 111, the transfer material 502, the draining material 211, and the second absorbent material 311. A capture element 411 is disposed between the cover material and the draining material 211, it is thus maintained in place on the upper surface of this draining material.

FIG. 4 illustrates another embodiment of the device 10. In this embodiment, the draining material comprises two separate segments, one upstream segment 211a and one downstream segment 211b. The device in addition comprises a conjugate material 501a disposed astride these two segments in order to, on the one hand, force the fluid to pass through the conjugate material 501a and on the other hand, ensure the fluid continuity between the receiving zone 100 and the reservoir zone 301. The downstream segment of the draining material 211b comprises a detection zone 600 including a detection pattern that is constituted of two lines 601 and 602 intended for detecting the presence or absence of a targeted analyte, and for revealing the total migration of the fluid in order to validate the test. The capture element 411 is disposed on the first segment 211a of draining material, upstream from the conjugate material 501a.

FIG. 5 illustrates another embodiment of the device 20 comprising two zones of migration 201, 202 situated on either side of a receiving zone 100 and two reservoir zones 301, 302 at the respective ends of the zones of migration. This device therefore comprises a first and a second lateral flow in opposite directions, represented by the arrows F1 and F2 shown in FIG. 5.

The first lateral flow F1 includes, as previously described here above, in fluid continuity with the first absorbent material 111 and from upstream to downstream in the direction of the arrow F1, a first conjugate material 501a, a first draining material 211 in contact with the first conjugate material, this first draining material comprising a first detection zone 600a and a second absorbent material 311 forming the first fluid reservoir.

The second lateral flow F2 comprises, in fluid continuity with the first absorbent material 111 and from upstream to downstream in the direction of the arrow F2, a transfer material 502a, a second draining material in the form of a first segment 212a and a second segment 212b of the draining material; a capture element 411 is disposed on the first segment; a second conjugate material 501b is disposed astride the two segments; the second segment 212b includes a second detection zone 600b. A second absorbent material 312 forming the second reservoir is finally in fluid continuity with the second segment 212b.

The second conjugate material 501b comprises second conjugate particles that are capable of binding on to an analyte that is sure to be found in the fluid. In this way, the detection of these second conjugate particles in the second detection zone 600b signifies that the fluid has at least passed beyond the first segment 212a of draining material and that as a consequence thereof the capture element 411 has been able to capture the one or more analyte(s) of interest.

Figure 6A:
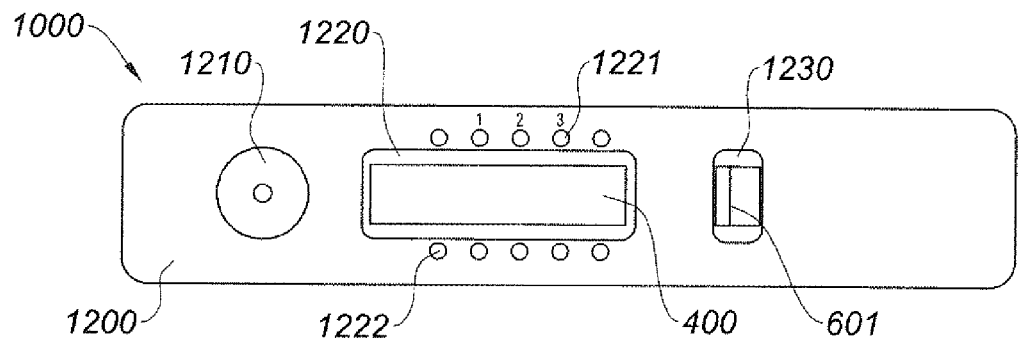
FIGS. 6A and 6B represent in top view and in exploded view one embodiment of an enclosure wherein a device is located.
Figure 6B:
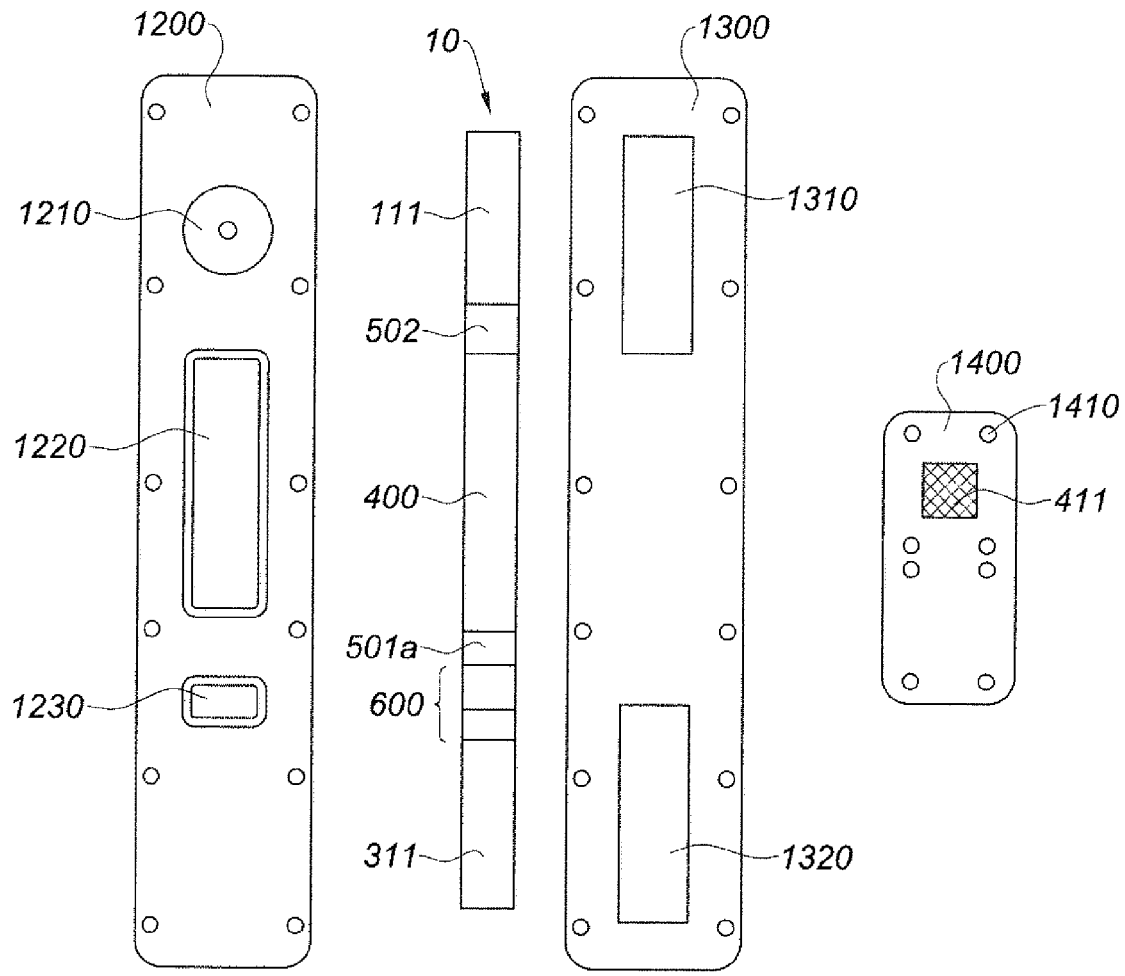

FIGS. 6A and 6B represent a sampling system comprising a device 10 and an enclosure 1000 wherein the device is located.

The enclosure is present in the form of a rod having an upper portion 1200 and a lower portion 1300, with these two parts being joined together, in use, for example by means of clipping and/or bonding; when these two parts are joined together, they enclose the device 10. FIG. 6A represents the external surface of the upper portion 1200, FIG. 6B represents the open device, that is to say, the internal surfaces of the upper and lower portions.

The upper portion 1200 comprises in succession:
- a first opening 1210, which is located so as to be facing the first absorbent material 111 of the device; this first opening is intended to receive the fluid sample and convey it to the first absorbent material;
- a second opening 1220 of elongated form, positioned so as to be facing the draining material 211;
- a first window 1230, positioned so as to be facing the detection zone 600 of the device; this window may be open and forming a third opening, or may comprise a translucent material that makes possible the reading of a detection signal 601.

The lower portion 1300 includes the recessed housings 1310 1320 provided for receiving and maintaining in place the device 10.

The system includes in addition a plate 1400 comprising a capture element 411 on one of its surfaces. The plate is provided so as to be secured at least temporarily, for example by clipping, on to the edges of the second opening 1220 in such manner that the capture element comes in contact with the draining material 211 through the second opening 1220. To this end, the upper portion 1200 of the enclosure and the plate 1400 comprise the means 1222, 1410 which cooperate, for example by means of clipping, in order to secure the plate on to the upper portion of the enclosure in a reversible manner, during the time of sampling. After the sampling, only this plate 1400 with the capture element thereof is sent to the analysis centre.

The upper portion 1200 of the enclosure 1000 also comprises graduations 1221 that are disposed along the second opening 1220 in order to guide the user in the positioning of the plate 1400 and thus of the capture element 411 on the draining material 211, this being dependent on the one or more analytes of interest sought.

Figure 7A:
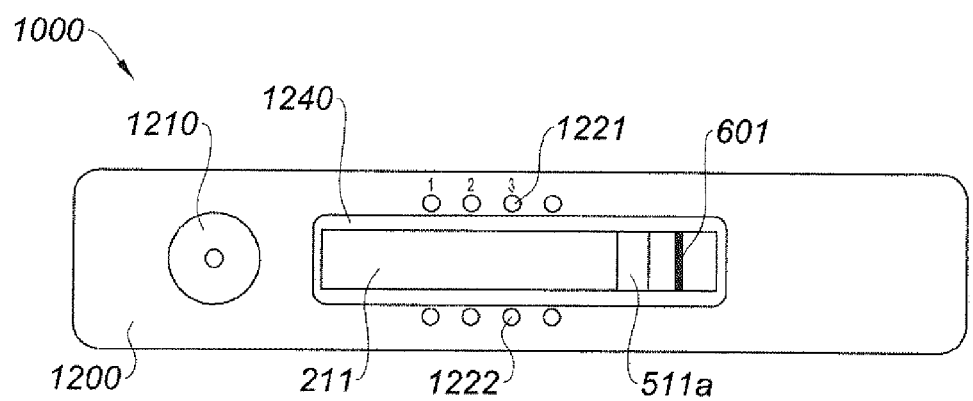
FIGS. 7A and 7B represent a top view of another embodiment of an enclosure wherein a device is located.

FIG. 7A illustrates a variant of the enclosure 1000 in which the second opening and the first window are merged into one single opening 1240, which makes apparent the conjugate material 511a.

Figure 7B:
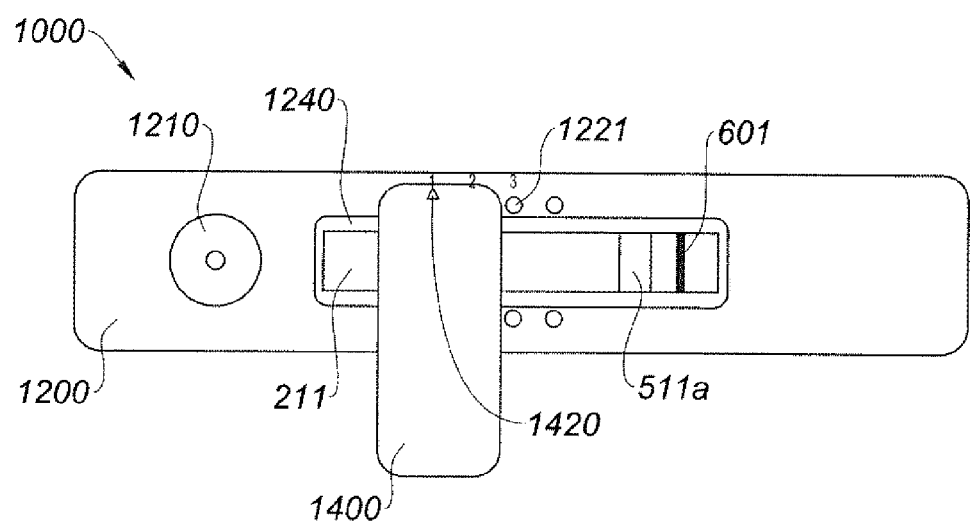

FIG. 7B illustrates a plate 1400 clipped on to the upper portion 1200 of the enclosure 1000; as has been seen here above, the plate comprises on the surface that is not visible in FIG. 7B a capture element 411 which is found to be thus brought into contact with the draining material 211 with a view to the sampling of an analyte. The visible surface of the plate 1400 includes a reference mark or pin 1420 which is disposed to be facing a graduation 1221 of the upper portion 1200.

FIGS. 8A and 8B represent another embodiment of an enclosure 2000 adapted to the double flow device 20 as illustrated in FIG. 5. As in the earlier instance, the enclosure is present in the form of a rod having an upper portion 2200 and a lower portion 2300, with these two parts being joined together, in use, for example by means of clipping and/or bonding; when these two parts are joined together, they enclose the device 20. FIG. 8A represents multiple views of the external surface of the upper portion 2200, FIG. 6B represents the open device, that is to say, the internal surfaces of the upper and lower portions.

The upper portion 2200 comprises:
a first opening 2210, which is located so as to be facing the first absorbent material 111 of the device; this first opening is intended to receive the fluid sample and convey it to the first absorbent material, and on either side of this first opening:
a first window 2220, positioned so as to be facing the detection zone 600a of the draining material 211; this window may be open and forming a second opening, or may comprise a translucent material that makes possible the reading of detection signals 601, 602;
a second window 2230, positioned so as to be facing the detection zone 600b of the second segment of draining material 212b; this window may be open and forming a third opening, or may comprise a translucent material that makes possible the reading of the detection signal 603.

In the embodiment illustrated, the enclosure 2000 also includes a cut-off line or fragile part 2240 situated between the first opening 2210 and the second window 2230, that makes it possible to easily split/divide the enclosure 2000 into two parts, a first cleavable part 2000a comprising the capture element 411, and a second part 2000b.

As can be seen in FIG. 8B, the upper portion 2200 of the enclosure includes, on its interior surface, a capture element 411 situated between the cut-off line 2240 and the second window 2230, visible by transparency in FIG. 8A. When the enclosure contains a device 20, the capture element 411 comes into contact with a first segment 212a of draining material.

In this manner, after sampling of the one or more analytes of interest, the first cleavable part 2000a, comprising the capture element 411, is separated from the second part 2000b of the enclosure, and only the first part is sent to the analysis centre for assaying of the analytes.

Figure 9A:
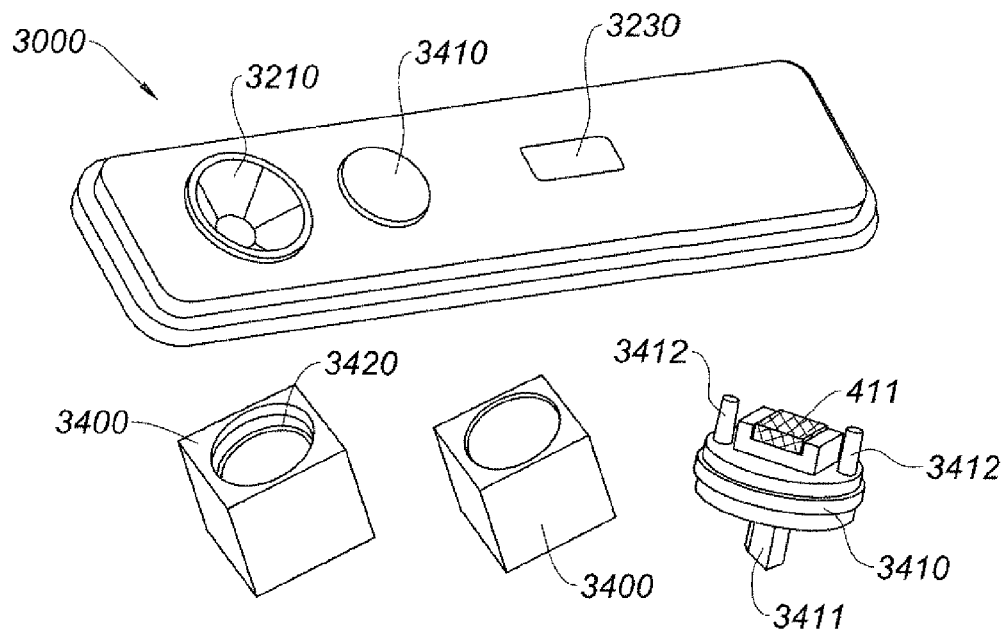
FIGS. 9A and 9B represent in perspective and in exploded view a system including an enclosure and a capsule for holding a capture element.
Figure 9B:
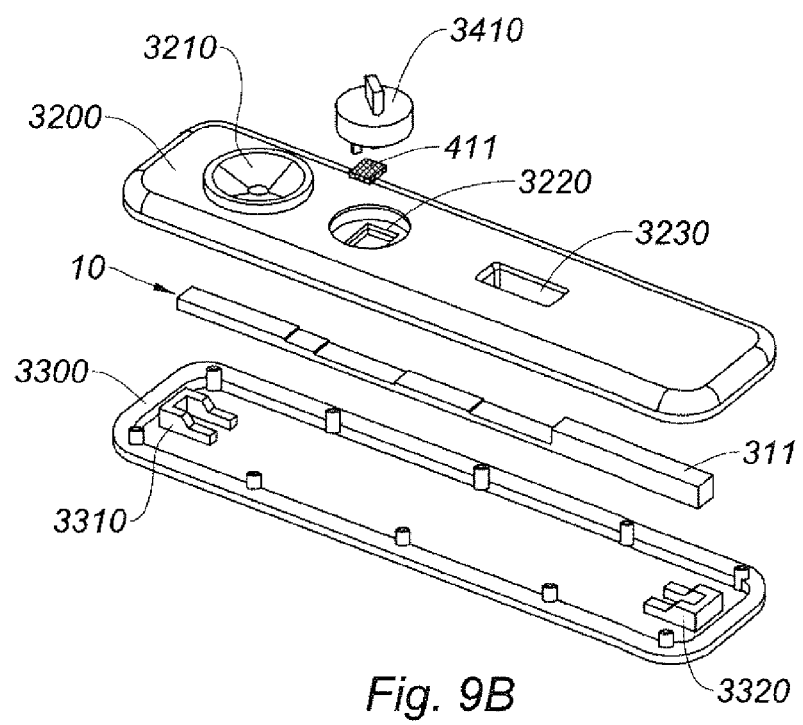

FIGS. 9A and 9B illustrate a variant of the sampling system comprising an enclosure 3000 within which are located a device 10 and a capsule 3400.

The enclosure 3000 is similar to the enclosure 1000 of FIGS. 6A and 6B. It comprises an upper portion 3200 and a lower portion 3300 which, when they are joined together, enclose a device 10.

The upper portion 3200 comprises in succession:
a first opening 3210, which is located so as to be facing the first absorbent material 111 of the device;
a second opening 3220 of circular shape, positioned so as to be facing the draining material 211 which will subsequently be detailed here below;
a first window 3230, positioned so as to be facing the detection zone 600 of the device.

The lower portion 1300 includes the recessed housings 3310, 3320 provided for receiving and maintaining in place the device 10.

The system in addition includes a container or capsule 3400 comprising a cap 3410. This cap comprises, on one surface referred to as upper surface an operating handle 3411, and on one surface referred to as under surface:
two pins or lugs 3412, in such manner that the cap 3410 is capable of being secured (by screwing, clipping, interlocking or otherwise) both on to an opening 3420 of the capsule and on the second opening 3220 of the enclosure 3000, it being possible for the modes of securing on to the container 3400 and on the enclosure 3000 to be different;
a capture element 411.

In this embodiment, the capture element 411 is supplied enclosed in the capsule 3400, it is removed therefrom with the cap 3410, this cap is secured on the enclosure 3000 for the time period of the sampling. When sampling is completed, the cap is detached from the enclosure and re-placed back on the capsule 3400. The capsule alone is sent to the analysis centre. The advantage is that the operator never has to touch the capture element 411 which thus remains free of any contamination.

This description is not intended to be limiting. Thus:
the device may not be rectilinear as shown in the figures; in particular, in the embodiment with two lateral flows, these two flows may share the same given fluid reservoir (storage) zone;
the enclosure does not necessarily comprise the cut-off line 2240, the enclosure in its entirety may be sent to the laboratory;
although the FIGS. 6A to 9B illustrate only the systems in which the capture element 411 is detachable from the enclosure 1000, 2000, 3000, these systems could possibly include a device in which the capture element is not easily detachable from the draining material, as is illustrated in FIGS. 2 and 3.

The following experimental examples illustrate certain aspects of the invention without however limiting its scope.

EXAMPLE 1

Figure 10A:
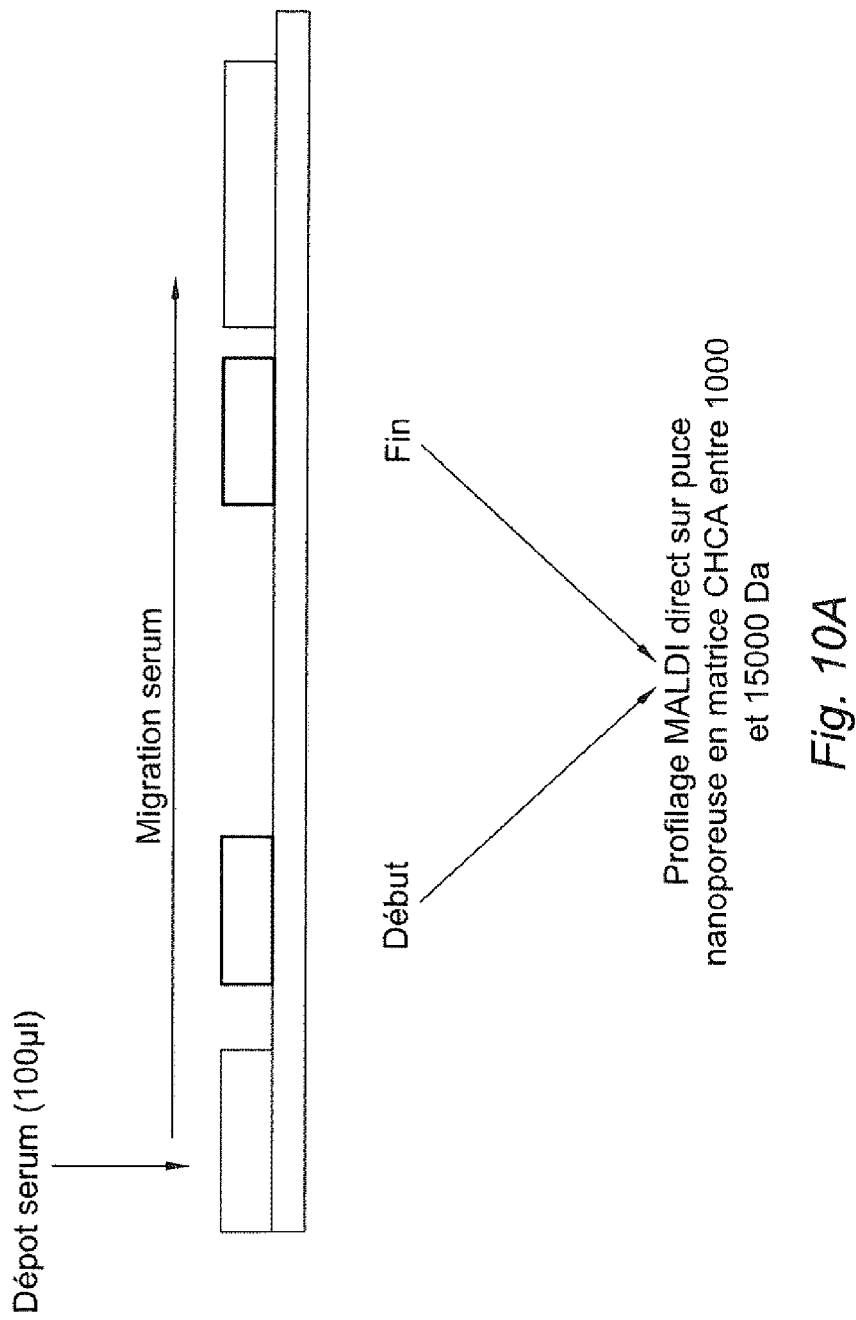
FIGS. 10A and 10B represent the comparison of profiles from mass spectrometry MS on nanoporous silicon between the beginning and the end of the migration of the serum on the test strip. Detection threshold: S/N (signal to noise ratio) of at least 3.

Comparison of Profiles from Mass Spectrometry (MS) on Nanoporous Silicon Between the Beginning and the End of the Migration of the Serum on the Test Strip The experimentation conditions are described in the diagram shown in FIG. 10A. Briefly, two nanoporous silicon chips of the same dimensions (5×5×0.75 mm, 1 µm of porosifying thickness on the surface, pores of 20 nm section and degree of porosity of the order of 50%) were deposited on a nitrocellulose strip, the one adjoined just after the receiving zone 111 (zone A) and the other adjoined just before the absorbent material 311 (zone B) of the receiving zone. After the depositing of 100 µl of serum and migration to the reservoir zone, the two chips were collected, rinsed 3 times with water before performing a MALDI (matrix-assisted laser desorption/ionization) analysis directly on the chip, with CHCA (α-Cyano-4-hydroxycinnamic acid) matrix, between 1000 and 15000 Da.

Figure 10B:
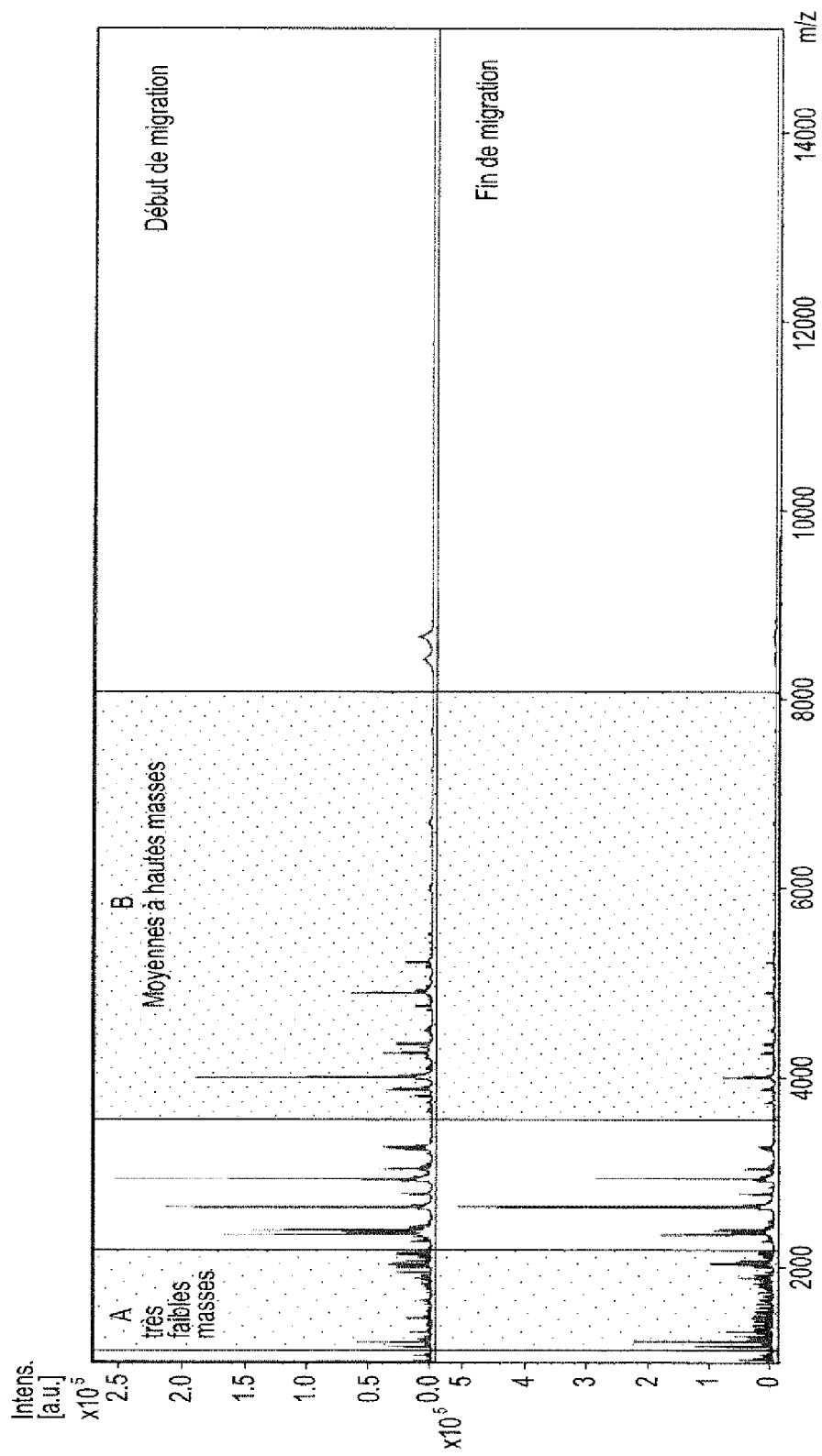

The results, illustrated in FIG. 10B and in Table 1 here below, suggest an effect of separation of the proteins by size exclusion chromatography during the migration of the serum on nitrocellulose. Indeed, it is observed that on the porous material at the start of migration there are fewer peaks (46)

with a high signal/noise ratio for masses with values less than 2400 Da as compared to the porous material at the end of migration (68). This observation is reversed for masses above 3500 Da. The nitrocellulose mesh thus acts as a chromatographic surface, enriching the molecules of lower molecular weight during the migration.

TABLE 1

|  | Number of peaks detected with a high signal/noise ratio | |
| --- | --- | --- |
|  | Mass A Zone (1000-2200 Da) | Mass B Zone (3500-9000 Da) |
| Capture element (porous) at the start of migration | 46 | 31 |
| Capture element (porous) at the end of migration | 68 | 20 |

The MALDI detection being sensitive to these specific enrichments, the signal/noise ratios for each mass range are changed as well as the spectral detection thereof.

EXAMPLE 2

Study of Stabilisation of Molecules Trapped in the Nanoporous Silicon Over 21 Days The nanoporous silicon chips used here are identical to those described in Example 1. Ten microlitres of serum were deposited directly on each chip, and thereafter the following steps were carried out:
  incubation of the serum on porous: 10 min;
  rinsing 3× with distilled water;
  storage in bag with desiccant (silica gel) at ambient temperature and at 37° C. (atmospheric humidity);
  direct MALDI profiling with CHCA between 1000 to 15000 Da every 7 days.

Figure 11:
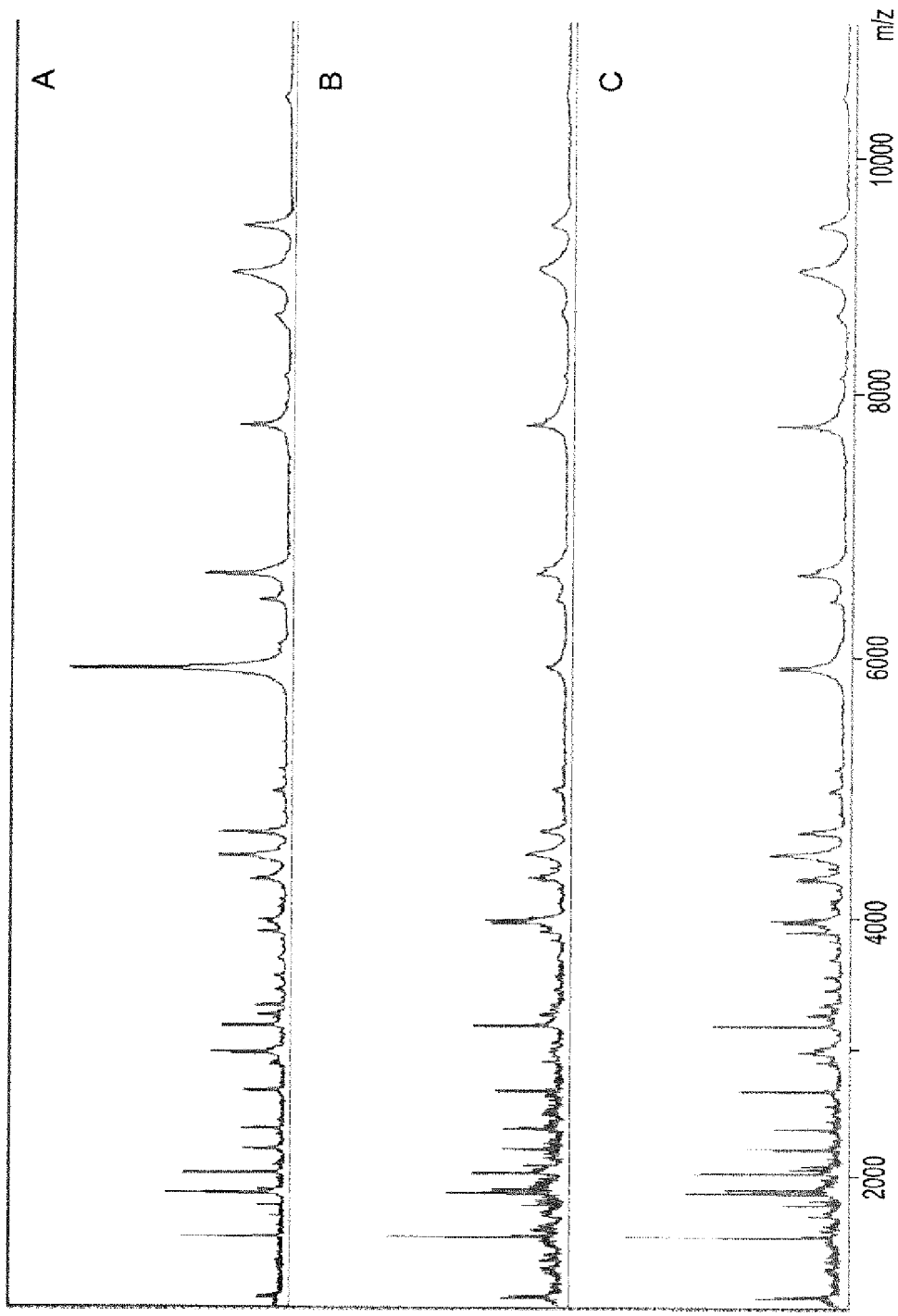
FIG. 11 represents the comparison of the profiles of serum on nanoporous silicon on D0 (line A), D21 at ambient temperature (line B) and D21 at 37° C. (line C)

The results, illustrated in FIG. 11, show that the profiles are comparable in terms of species detected. No degradation product is observable. The correlation of spectral characteristics between the different storage conditions (FIG. 12), as well as the correlation of profiles between D0 and D21 (at ambient temperature or at 37° C., FIG. 13) is greater than 0.75.

In FIG. 12, the unit of the Y axis is the correlation index, the value 1 being a perfect correlation.

In FIG. 13, the unit of the X and Y axes is the intensity of the detected peaks (points) normalised by log 10.

The invention claimed is:

1. A lateral flow device for the sampling of at least one analyte of interest in a fluid, which includes:
  a fluid receiving zone for receiving the fluid, comprising a first absorbent material that is capable of collecting the fluid;
  at least one zone of migration for migration of the fluid, extending between a first end and a second end, each zone of migration including a draining material in fluid continuity with the first absorbent material, the draining material being capable of collecting the fluid absorbed by the receiving zone and of draining the fluid from its first end to its second end;
  at least one fluid reservoir zone comprising a second absorbent material in contact with the draining material at the level of the second end of each fluid migration zone, the second absorbent material being capable of absorbing the fluid drained by the draining material; and
  a detection means between the receiving zone and the reservoir zone, that provide the ability to determine a presence or absence of the said one or more analyte(s) of interest in the sample,
  wherein said draining material comprises two separate segments, at least the one of the said zones of migration further comprises at least one capture zone, the device further comprising a capture element that is applied on to each capture zone, against one of the separate segments of the draining material between the first end and the second end thereof, each capture element comprising a nanoporous or mesoporous silicon material and being capable of capturing the analyte of interest present in the fluid, each capture element being adapted so as to be separated from the draining material, the device comprising a first conjugate material disposed astride the two segments of the draining material so that a fluidic continuity is ensured between the receiving zone and the reservoir zone, the said conjugate material comprising conjugate particles that are capable of binding to the analyte(s) of interest.

2. The lateral flow device according to claim 1, wherein the detection means include:
  at least one second conjugate material disposed to be in contact with the draining material, the said conjugate material comprising conjugate particles that are capable of binding to the analyte(s) of interest; and
  a material that is capable of immobilsing the conjugate particles bound to an analyte of interest and of revealing them, the said material impregnating at least one zone of detection of the draining material.

3. The lateral flow device according to claim 1, wherein it comprises a first zone and a second zone of migration respectively including a first draining material and a second draining material, the receiving zone being situated between the said two zones of migration.

4. The lateral flow device according to claim 1, wherein the first absorbent material and/or the second absorbent material are made of a fibrous material.

5. The lateral flow device according to claim 1, wherein the receiving zone comprises in addition a transfer material.

6. The lateral flow device according to claim 3, wherein at least one of the draining materials comprises a nanoporous or mesoporous material.

7. The lateral flow device according to claim 2, wherein the capture zone is located upstream from the first conjugate material in a direction of a drainage of the fluid in the draining material.

8. The lateral flow device according to claim 2, wherein at least one of the conjugate materials includes conjugate particles that are capable of binding to an analyte which is certain to be found in the fluid.

9. The lateral flow device according to claim 1, wherein the first absorbent material, the draining material, and the second absorbent material are disposed on a support or carrier material.

10. The lateral flow device according to claim 1, wherein it further includes a cover material that is capable of covering at least a portion of the receiving zone, the zone of migration and/or the fluid reservoir zone.

11. The lateral flow device according to claim 1, wherein the capture element is maintained in place against the draining material.

12. A sampling system for sampling analytes of interest in a fluid, wherein it includes an enclosure wherein is located the lateral flow device according to claim 2 comprising a single zone of migration, the said enclosure including:
- a first opening disposed so as to be facing the receiving zone of the said device;
- a first window disposed so as to be facing the detection zone in order to ensure an ability to read a detection signal.

13. A sampling system for sampling analytes of interest in a fluid, wherein it includes an enclosure wherein is located the lateral flow device according to claim 2 comprising two zones of migration, the said enclosure including:
- a first opening disposed so as to be facing the receiving zone of the said device;
- a first window disposed so as to be facing a first detection zone in order to ensure an ability to read a first detection signal;
- a second window disposed so as to be facing a second detection zone in order to ensure an ability to read a second detection signal.

14. The sampling system according to claim 12, wherein the enclosure in addition comprises a second opening disposed so as to be facing the capture zone of the device, in a manner such as to be able to deposit the capture element on to the said capture zone and/or to remove it therefrom.

15. The sampling system according to claim 12, wherein the at least one capture element is maintained in place on the capture zone, the said at least one capture element being capable of capturing the analyte of interest present in the fluid.

16. The sampling system according to claim 14, wherein the capture element is attached to a detachable support that is detachable from the enclosure.

17. The sampling system according to claim 16, wherein the detachable support of the enclosure is one of the following:
- a plate that is capable of being secured at least temporarily on to edges of the second opening;
- a cleavable part of the enclosure;
- a cap that is capable of being secured both on a capsule and on the second opening.

18. A sampling method for sampling at least one analyte of interest in a sample, that includes the following steps:
- depositing the said sample on the receiving zone of a device according to claim 1; and
- waiting until the fluid has migrated to the fluid reservoir (storage) zone, characterised in that in case of the presence of the analyte of interest in the sample, as evidenced by the detection means, the said analyte is drawn into the capture element (411).

19. The method of sampling according to claim 18, wherein the device is included in a sampling system according to claim 12 and that at the conclusion of the step of migration of the fluid, the capture element (411) is separated from the rest of the device.

20. An assay method for assaying at least one analyte of interest in a fluid sample, comprising a sampling step for sampling of the said analyte by means of a sampling method according to claim 18, followed by a step of assaying the said analyte present in the capture element.

* * * * *